United States Patent [19]

Gutnick

[11] 3,996,933
[45] Dec. 14, 1976

[54] INTRAUTERINE CONTRACEPTIVE DEVICES AND PROCESSES

[76] Inventor: Morton Gutnick, 8329 Fairview Road, Elkins Park, Pa. 19117

[22] Filed: Oct. 14, 1975

[21] Appl. No.: 621,958

Related U.S. Application Data

[63] Continuation-in-part of Ser. No. 432,435, Jan. 11, 1974, Pat. No. 3,913,573, which is a continuation-in-part of Ser. No. 294,200, Oct. 2, 1972, abandoned.

[52] U.S. Cl. .............................. 128/130; 128/260
[51] Int. Cl.² .......................................... A61F 5/46
[58] Field of Search .................... 128/127–131, 128/260; 424/22, 26, 28, 16

[56] References Cited

UNITED STATES PATENTS

| | | | |
|---|---|---|---|
| 812,770 | 2/1906 | Pond | 128/130 |
| 889,154 | 5/1908 | Rolfson-Schmidt | 128/130 |
| 1,395,295 | 11/1921 | Pond | 128/130 |
| 2,020,107 | 11/1935 | Cruickshank | 128/130 |
| 3,256,878 | 6/1966 | Schwartz et al. | 128/130 |
| 3,425,411 | 2/1969 | Robinson | 128/130 |
| 3,527,220 | 9/1970 | Summers | 128/130 |
| 3,545,439 | 12/1970 | Duncan | 128/130 |
| 3,640,269 | 2/1972 | Delgado | 128/130 |
| 3,656,483 | 4/1972 | Rudel | 128/264 |
| 3,659,596 | 5/1972 | Robinson | 128/130 |
| 3,692,027 | 9/1972 | Ellinwood | 128/130 |
| 3,710,795 | 1/1973 | Higuchi et al. | 128/260 |
| 3,779,241 | 12/1973 | Vennard et al. | 128/129 |
| 3,796,217 | 3/1974 | Arlen | 128/130 |
| 3,805,777 | 4/1974 | Ansari | 128/130 |
| 3,807,395 | 4/1974 | Chaft | 128/130 |
| 3,815,600 | 6/1974 | Groves | 128/130 |
| 3,845,770 | 11/1974 | Theeuwes et al. | 128/260 |
| 3,896,819 | 7/1975 | Zaffaroni | 128/130 |
| 3,918,443 | 11/1975 | Vennard et al. | 128/130 |
| 3,938,515 | 2/1976 | Leeper et al. | 128/260 |

*Primary Examiner*—Lawrence W. Trapp
*Attorney, Agent, or Firm*—Robert S. Bramson

[57] ABSTRACT

An intrauterine contraceptive device comprising an elongated shank having divergent convoluted portions at its distal end, said convoluted portions being generally sinusoidal in nature, said device having incorporated in said shank a permanent magnet and having a substantial portion of its surface covered with a biologically inert, silicone elastomeric material which may contain an analgaesic or anti-fertility agent which is gradually eleased in utero. In a preferred embodiment of the invention, the proximal end, of the shank contains a pair of downwardly extending divergent, resilient legs which tend to prevent inadvertent expulsion of the device. In another preferred embodiment, the lower end of the device is also formed with one or more small refillable containers for certain types of medication which are released gradually into the vagina and the lower end of the uterus over a prolonged period of time for the prevention and cure of such venereal diseases as gonorrhea, syphilis, trichomonas vaginalis and moniliasis.

5 Claims, 13 Drawing Figures

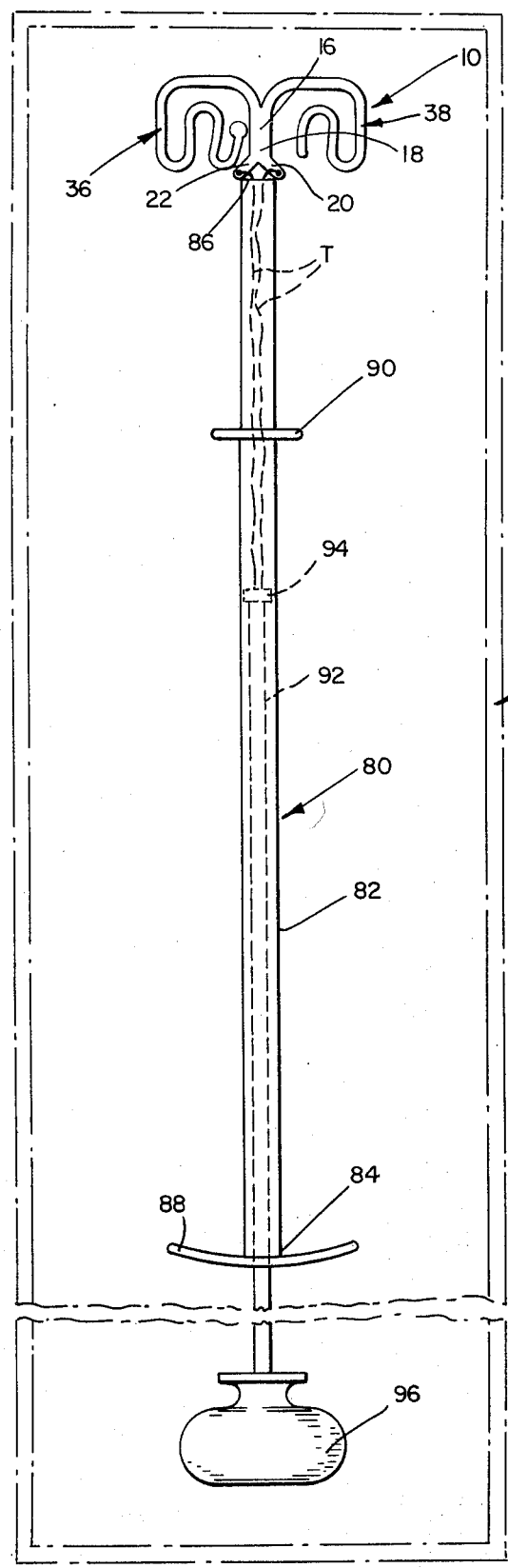
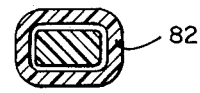
Fig. 5
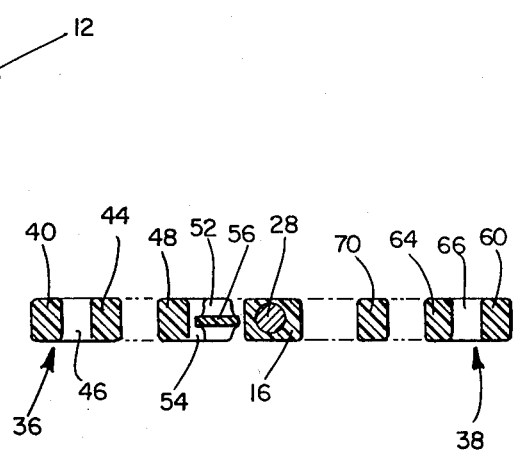
Fig. 6
Fig. 7

INTRAUTERINE CONTRACEPTIVE DEVICES AND PROCESSES

REFERENCE TO RELATED CASE

This is a continuation-in-part of United States Patent Application Ser. No. 432,435, filed Jan. 11, 1974, and now U.S. Pat. No. 3,913,573 which in turn is a continuation-in-part of United States Patent Application Ser. No. 294,200, filed Oct. 2, 1972, now abandoned.

BACKGROUND OF THE INVENTION

1. Field of the Invention

The invention relates to both new and useful improvements in contraceptive devices for human beings and other animals which serve also to prevent and cure venereal and other diseases.

2. State of the Art

It has been known for many years that a foreign object in the uterus will prevent conception. To date, many different types of intrauterine contraceptive devices, also known as IUDs, have been proposed, and several types are in widespread use, but none have been fully satisfactory.

Bleeding and pain account for eighty-five per cent of the complications or side effects of intrauterine contraceptive devices. Therefore, any device that would reduce or eliminate bleeding and pain would lead to fewer removals of intrauterine contraceptive devices for "cause," and would allow a greater percentage of patients to "continue to use" the IUDs and would probably also expand the usage of IUDs.

Lack of confidence in the IUDs, as a result of unnoticed spontaneous expulsion of the device with the resulting potential for unwanted pregnancy, or the improper positioning of the device resulting in a loss of the thread or threads in the uterus, continue to plague the presently available intrauterine contraceptive devices. When the tail of a conventional IUD cannot be seen at the cervical os, the physician is faced with a dilemma, since he must make a distinction between unnoticed expulsion, ascent of the tail into the uterine cavity and possible perforation of the uterus. With presently available IUDs, in order to determine their presence within the uterine cavity, the physician must either send the patient for an X-ray, with its attendant expense, radiation exposure, the possibility of the patient being pregnant, and additional loss of confidence in the IUD by the patient, or probe "blindly" in the uterus, with a sound, a long, thin metal instrument, and with nothing to guide the sound this can become a painful, difficult and even dangerous procedure.

Syphilis, gonorrhea, trichomonas vaginalis and moniliasis can be extremely harmful diseases, if not controlled, and are presently of epidemic proportions. No adequate technique for preventing, treating or curing these diseases has been demonstrated, although it is well-known that certain antibiotics and/or trichomonacides or moniliacides will kill the organisms that cause these diseases. Accordingly, it is extremely desirable to be able to kill any gonoccocus or syphilitic or other venereal disease-causing organisms immediately as they are transmitted in order to prevent either disease from developing in the host individual. It is particularly desirable to combine the contraceptive function of an IUD with a means for preventing and controlling venereal disease, and this goal is enhanced by the provision of means to prolong the release of anti-venereal disease medication without the necessity for removing the IUD.

BRIEF SUMMARY OF THE INVENTION

The invention comprises an IUD which may have a shank portion in which there is embedded a permanent magnet, the shank portion terminating at its distal end in a pair of convoluted loops having substantially transverse arms or arm segments with respect to the axis of the shank and sinusoidal arms extending laterally from the shank. One of the convoluted loops may be longer than the other in the elongated position in which the loop is coextensive with the shank, and may terminate in a bulbous end portion. In one embodiment, the transverse arms are connected to the shank and the convoluted loops depend therefrom. In another embodiment, the convoluted loops are connected to the shank and the transverse arm are connected to the outer ends of the respective convoluted loop members. Each of the convoluted loops is substantially sinusoidal in configuration and comprises at least three linear segments substantially parallel to the shank and connected by the transverse arm to the shank. The IUD is formed of a flexible thermoplastic material having plastic memory, so that the convolutions may be straightened out and the IUD placed into an elongated tube for proper uterine insertion by a physician or other medical professional.

In a preferred embodiment of the invention, the arms and convolutions and a substantial portion of the shank are formed of or covered with a thin coating of a material which does not cause foreign body reactions, even after prolonged periods of time, and minimizes bleeding from contiguous areas, such as a silicone rubber, to lessen the incidence of any problems, such as bleeding, resulting by the residence of the IUD in utero.

In a preferred embodiment of the invention the proximal end of the shank terminates in a pair of downwardly extending divergent flexible legs, which serve to retain the IUD in place and prevent expulsion. The legs form an acute angle in the range from about 6° to about 30°, and preferably about 10°. The proximal end of the shank, or, in the case of the preferred embodiment, the ends of the divergent legs, terminate in a small nodular segment or segments to which a thin filament or thread is fastened to extend from the uterus into the vagina and provide a tangible manifestation of the presence of the IUD in situ.

The permanent magnet which is incorporated in the shank of the IUD serves two functions. First of all, it prevents inadvertent expulsion of the IUD from the uterus because it is positioned at the top of the shank, thereby making the IUD top heavy and less likely to be expelled, and because the use of the magnet allows the IUD to be located by the use of a ferrous "sound" or a magnetic or electromagnetic "sound" so that the physician, when he is probing in the uterus to locate the IUD will be able to do so by virtue of the attraction of the ferrous or magnetic or electromagnetic sound to the magnet incorporated in the IUD.

The IUD preferably has incorporated therein a sufficient amount of barium or a barium salt to make the IUD radio-opaque whereby it may be located by X-ray, if necessary.

In an embodiment of the invention, a medication, such as a topical anesthetic or other pain relieving drug or an antifertility agent, may be incorporated into the silicone rubber material of the IUD, and will be leached out therefrom, to permit a controlled release of drug into the uterus during the initial and subsequent periods of use of the IUD.

In an alternate embodiment of the invention, the convolutions of the IUD are wrapped with fine copper wire, in order to improve the efficacy of the IUD in preventing conception.

In yet another embodiment of the invention, one or more containers for liquid medication, which may be a single compartmented container, are formed within the shank portion of the IUD, preferably at its lower end, and terminating in a self-sealing globule which will gradually release the liquid medication into the uterus or vagina. The shank of the IUD can be formed to extend through the cervix into the vagina and can therefore release medication directly into the vagina. This embodiment is particularly useful for the release of certain antibiotics, such as penicillin, erythromycin or tetracycline, which will prevent or cure syphilis, and gonorrhea, and trichomonacides and moniliacides for the prevention and cure of trichomonas vaginalis and/or moniliasis. The material of the globule, which permits the gradual release of medication therefrom, also permits the resealable introduction of a fine hypodermic needle therein to refill the container or containers with medication and thereby to avoid the necessity for removing the IUD and inserting a substitute IUD. The size of the globule, and the attendant rate of release of medication therefrom, can be varied to release the minimal inhibitory concentration of antibiotic necessary to inhibit the growth of the particular gonococcal or other disease-causing strain of organism in the country of use, it being well recognized that strains in some geographic areas are more virulent than the strains present in other areas. In the embodiment utilizing two containers formed in the shank of the IUD one may contain a trichomonacide or moniliacide, while the other may contain the antibiotic.

OBJECTS OF THE INVENTION

An object of this invention is to provide an intrauterine contraceptive device which is safe and effective in comparison to the prior art devices.

Another object of this invention is to provide an IUD which will spread over most of the endometrial cavity and thus lessen the chances of pregnancy.

Still another object of this invention is to provide an IUD which, once placed properly, will remain relatively fixed in its intrauterine position and will not easily be expelled inadvertently, but which can readily be removed when removal is desired.

A concomitant object of this invention is to provide an intrauterine contraceptive device whose presence and proper position in the uterus can be readily determined by the use of a ferrous, magnetic or electromagnetic sound.

Another object of the present invention is to provide an IUD which is less likely to be expelled inadvertently than prior art devices.

Yet another object of the present invention is, when possible and medically advisable, to provide an IUD construction which can be retrieved by an electromagnet in order to save the patient an abdominal operation in cases of partial perforation of the uterus.

Still another object of this invention is to provide an IUD formed with a medically acceptable outer material to minimize uterine bleeding due to a foreign material in the uterus.

Yet another object of this invention is to provide an IUD construction which incorporates topical anaesthetics, steroids or medicaments, when medically advisable, in the material of the IUD for the slow release of pain relieving drugs or anaesthetics in utero.

It is similarly an object of this invention to provide an IUD which is of unique mechanical design, which can be worn with comfort for years, and then easily removed without discomfort to the patient.

A further object of this invention is to provide an IUD that may be pre-sterilized, that lends itself to easy insertion into the uterus with the help of a simple instrument, and that will not interfere with either menstruation or vaginal function.

An additional object of this present invention is to provide an IUD which a nulliparous patient can use effectively with no or minimal discomfort, thereby to expand the number of potential users of IUDs.

Another object of this invention is to provide an IUD that will release medication into the uterus or vagina at a controlled rate over a prolonged period of time for the prevention or treatment of diseases, such as syphilis and gonorrhea.

Yet another object of this invention is to provide an IUD that will release medication directly into the vagina and can be refilled with medication without removing the IUD from the uterus.

A concomitant object of this invention is to provide an IUD which will release more than one kind of medication into the uterus and/or vagina from a plurality of refillable compartments.

Still another object of this invention is to provide a process which will serve the dual function of long term contraception and long term prevention and cure of venereal diseases effectively, safely and economically, and an apparatus for that process.

DESCRIPTION OF THE DRAWINGS

FIG. 5 is a cross-sectional view, taken along line 5—5 of FIG. 1;

FIG. 6 is a cross-sectional view, taken along line 6—6 of FIG. 3;

FIG. 7 is a front elevational view of the preferred embodiment of the invention, and the insertion device, as packaged prior to use;

DETAILED DESCRIPTION OF THE INVENTION

Figure 2:
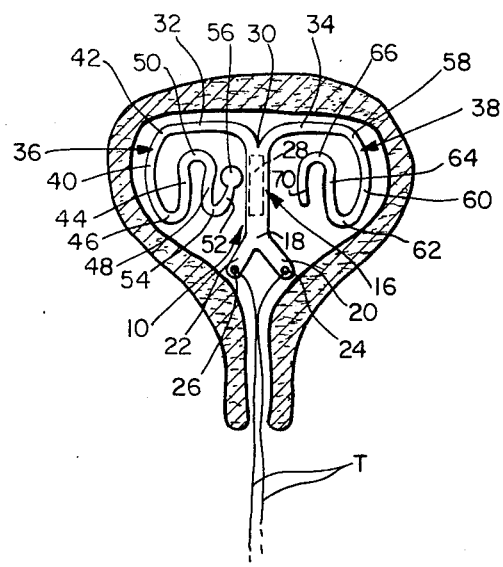
FIG. 2 is a front elevational view of the preferred embodiment of the IUD of this invention, located in utero in its position of use.

Viewing FIG. 2, the preferred embodiment of the intrauterine contraceptive device of this invention, which is generally designated by numeral 10, is seen to comprise a thin, elongated central stem or shank 16, of generally rectangular cross-section with rounded corners, although this shape may also be elliptical or oval. At the proximal end 18 of the shank 16, there is formed a pair of downwardly extending, divergent flexible legs, respectively designated by numerals 20 and 22. The legs are preferably integrally formed with the shank 16, and extend at angles in the range from about 3° to about 15°, and preferably about 5°, with respect to the vertical. Therefore, the angle between legs 20 and 22 is in the range from about 6° to about 15° and is preferably about 10°. At the proximal extreme of each of the two legs 20 and 22 is located an eye or nubbin, respectively designated as 24 and 26, to which filaments or tails, designated by the letter T, are fastened, as by knotting, through an aperture therethrough, fusion, or by means of a suitable medically acceptable adhesive.

Embedded within shank 16 is a permanent magnet 28, which, in the preferred embodiment, occupies at least 50% of the length of the shank 16, and preferably occupies approximately the upper two-thirds of the length of the shank 16. The permanent magnet also occupies at least 80% of the cross-section of shank 16, in the preferred form of the invention, so that the thermoplastic material of shank 16 only provides a thin covering layer for the permanent magnet 28.

The distal end 30 of intrauterine device 10 is integrally formed with a pair of divergent arms 32 and 34, which extend in a transverse direction with respect to the axis of shank 16. Each of the arms 32 and 34 is a part of a convolute or loop section, respectively designated by numerals 36 and 38. Viewing convolute section 36, it is seen to comprise the arm 32, a depending leg 40 connected to arm 32 by curved section 42, and upwardly and substantially vertically extending leg 44 connected to leg 40 by curved section 46, a depending leg 48 connected to leg 44 by curved section 50, and an upstanding leg 52 connected to depending leg 48 by a curved section 54. Leg 52 terminates at its free end in an enlarged bulbous extremity or nodule 56, which may be of spherical or disc-shaped configuration, the purpose of which will be explained hereinafter.

Viewing convolute section 38, it is seen to comprise the transverse arm 34, which is connected by arcuate section 58 to depending leg 60, which is, in turn, connected by arcuate section 62 to upstanding leg 64. Upstanding leg 64 is connected by arcuate section 66 to depending leg 70.

It is to be noted that the corresponding legs of the convolute sections 36 and 38 are of approximately the same length, but that convolute 36 has an additional leg section 52 and connecting section 54, not present in convolute 38. Accordingly, when the convolute sections are stretched out to be substantially coextensive with the longitudinal axis of shank 16, leg 52 and its enlarged bulbous end 56 will extend beyond the leg 70. The purpose of having this longer leg and bulbous end is to facilitate the insertion of the IUD into the insertion member and its subsequent proper placement in the frontal plane of the uterine cavity. The bulbous end 56 is of greater cross-section than the aperture in the insertion member, which is described below, and prevents the IUD from being drawn completely into the insertion member. Bulbous end 56 also, because of its smooth and round leading edge, facilitates insertion of the IUD into the uterus and minimizes the likelihood of irritation of the walls of the cervical canal and of the uterus during the placement of the IUD.

In the preferred form of the invention for a patient, the shank 16 has a length of approximately 16 mm., a width of approximately 4 mm. and a depth of approximately 2.5 mm. Each of the legs 20 and 22 has a length of about 8 mm., a width of 2 mm. and a depth of 2.5 mm. The over-all dimensions of the IUD unit in situ are about 38 mm. wide and 26 mm. high. The permanent magnet 28 is 9 mm. long and 3 mm. in diameter. However, the dimensions given are for general guidance only, and may be varied to suit the needs of the patients and to accommodate best the largest number of patients.

Each of the convolute sections, in cross-section, has a rounded-corner rectangular configuration, and has a width of 2 mm. and a depth of 2.5 mm., and when straightened out so that the convolute legs are substantially coextensive with shank 16, the entire unit has a length of approximately 100 mm.

For a nulliparous patient, the IUD of this invention would preferably have somewhat different dimensions. The permanent magnet would be of 2 mm. or less diameter, so that shank 16 would be about 2.5 mm. wide. The entire IUD unit would occupy a width of about 26 mm. and a height of about 26 mm.

The filaments or tails T are preferably round in shape, about 0.2 mm. in diameter and about 100 mm. in length and are preferably extrusions of nylon, polyethylene, polytetrafluoroethylene or other flexible, medically acceptable material. The tails T may be fastened to the nubbins 24 and 26, by tying, adhesive or fusion. The length of each of the filaments T is such that a substantial amount of residual length can be cut after the IUD is inserted so that a string of about 75 mm. remains in the vagina.

The foregoing dimensions as to the IUD device of this invention are not critical, but are optimum from a practical standpoint for proper, snug fit of the IUD in the endometrial cavity, and may be modified to suit the characteristics of the patients to be using the IUDs of this invention. However, it is to be noted that the IUD of this invention is designed to have minimum bulk to insure minimum likelihood of pain or discomfort on insertion. It is noteworthy that the IUD must be substantially planar in configuration, to allow it to conform properly to the shape of the uterus, which is thin and flat.

The shape of convolute sections 36 and 38 is of particular importance in the invention because it conforms substantially to the configuration of the endometrial cavity and spreads to occupy most of the endometrial cavity. Thus, the outer legs 40 and 60 and transverse arms 32 and 34 of the respective convolutes 36 and 38 should be substantially straight to conform to the shape of the walls of the endometrial cavity. The inner legs of convolutes 36 and 38, that is to say, legs 44, 48 and 52 of convolute 36 and legs 64 and 70 of convolute 38, are preferably substantially straight and parallel to shank 16. However, it is within the purview of this invention for those legs to be somewhat curved in configuration, the primary consideration being the necessity for occupying the maximum portion of the endometrial cavity.

Although the shank, legs, and convolute sections of IUD 10 are preferably of rounded corner rectangular cross-section, it is within the purview of this invention for these elements to be of oval or elliptical or other non-circular cross-section. Non-circular cross-section is desirable to insure that the IUD may properly be located in the correspondingly shaped insertion unit, to allow the IUD readily to be placed in the frontal plane of the uterus.

The intrauterine contraceptive device 10 is preferably formed of a resilient, biologically inert, medically acceptable material having plastic memory, i.e. resistance to cold flow, so that the device will resume its convoluted shape after it has been held in the elongated position in the insertion device for a reasonable period of time. The material of choice is polyethylene, and a selection of medically acceptable polyethylene of optimum molecular weight and other characteristics is within the purview of the skilled artisan. In molding the intrauterine device of this invention, it is desirable to add about 10% or more by weight of barium or a barium salt, in order to make the intrauterine device radioopaque, whereby it may be viewed by X-ray, in the event that the exact location of the IUD is required to be determined.

The device 10 is preferably covered, at least in areas other than those immediately overlying the magnet 28, with a thin layer of a medically acceptable silicone elastomer, such as Silastic, a product of Dow Chemical Company. It is also within the purview of this invention to incorporate medicaments, such as local anesthetics, and anti-fertility agents, such as steroids, in effective quantities into the silicone elastomer sheeting or coating which may then be leached out for gradual release into the uterus, in instances in which the introduction of such material is desirable, safe and efficacious.

When it is desired to incorporate a topical anesthetic into the Silastic, lidocaine, also sold under the trademark Xylocaine, is the anesthetic of choice. This anesthetic may be used in concentrations of up to 4% by weight, but is preferably in concentrations of 1 or 2 percent by weight. This anesthetic is stable and boilable, non-irritating to tissues, and the onset of anesthetic effect is immediate, diffusing rapidly into the tissues. The typical dose would maintain the anesthetic effect for about one to one and one-half hours.

It may be desired to desensitize both the cervical canal and the endometrial cavity prior to the insertion of the IUD of this invention, particularly in a nulliparous patient. This can conveniently be achieved by introducing or instilling about 1 cc. of one or two weight percent Xylocaine solution into the cervical canal and introducing or instilling about 2 to 4 cc. of Xylocaine solution into the uterine cavity. A suitable presterilized syringe, containing the proper concentration of anesthetic solution may be packaged in the same sterile sealed package as the intra-uterine device.

The electrical activity of the human uterus in the presence of an IUD has been measured, and it has been determined that there is marked uterine activity shortly after the introduction of the IUD. Increased uterine activity has been noted at the time of ovulation, and particularly at the time of menstruation. This is why the expulsion of an IUD is most likely to occur after or during menses.

The use of an anesthetic incorporated into the IUD of this invention can be quite helpful in reducing the frequency of expulsion of IUDs, a primary cause of ineffectiveness of IUDs in many patients. Irritation of the cervix and/or uterus upon insertion of the IUD, and the pain or discomfort associated therewith, substantially increases the likelihood of expulsion of IUDs. Therefore, incorporation into the silicone elastomer of a sufficient amount of a local anesthetic, such as lidocaine or Xylocaine will desensitize the cervix and uterus for a sufficient period of time after insertion of the IUD in utero to reduce the likelihood of IUD expulsion.

When it is desired to incorporate medication into the silicone elastomeric material of the IUD, this may be done in one of three ways. If the IUD is constructed primarily of a material such as polyethylene, the shank and other parts of the IUD may be covered with a sheet or spray coating of medical grade Silastic elastomer in which the medicament has been incorporated, in a matter to be discussed hereinafter. Alternatively, the shank of the IUD, or the entirety of the IUD, may be formed of medical grade Silastic elastomer, having the medicament incorporated therein.

Suitable medicaments for incorporating into the silicone elastomeric material are local anesthetics, such as Xylocaine or lidocaine, or anti-fertility agents, such as progesterone or medroxy progesterone acetate. If one of the progestogens is incorporated into the silicone elastomeric material, medication is released during the first few days of residence of the IUD in utero at a fairly rapid rate, and after the first few days of residence the drug continues to be released at a much slower, relatively constant rate for a prolonged period of time. Other steroids, such as estradiol, testostrone, cortisol and androstenedione, which are the more polar steroids, may also be used, but they are not released at as high a rate as the less polar steroids.

The medicament can be incorporated into the silicone elastomer by admixing with the silicone elastomer when it is in a fluid state, and subsequent formation of the amorphous or fluid elastomer into the element of the IUD by extrusion, die casting, or the like. Alternatively, the medicament may be incorporated in the elastomer, when the elastomer is in the fluid state, and sprayed in a fluid state onto all or selected portions of an IUD of a different material, such as polyethylene.

An alternative method for insertion of the medication is to place an amount in the range from between 50 to 500 milligrams of the medication, in the form of milled crystals, within a hollow tube of the silicone elastomeric material of medical grade. Such a tube would constitute all or part of the shank of the IUD of the invention, but the tube would have an outside diameter not substantially in excess of 3 to 4 millimeters. The open end of the tube would be sealed with a medical grade adhesive, such as a silicone rubber adhesive. The medication would then be leached out through the silicone elastomeric walls of the hollow tube. It is important to note that the rate of passage or diffusion of the medication through the Silastic wall is not influenced by the weight of medication contained therein; rather, its releases are dependent upon the surface area and wall thickness of the elastomeric material. That is to say, more medication will pass through a long tube than a short tube, and for a given amount of surface area, substantially more medication passes through a thin wall of material than through a thicker wall. The thickness of the wall and the surface area of the elastomeric tube can thereby be controlled in dimension to control the rate of release of medication.

It is also within the purview of this invention to incorporate more than one medication into the material of the invention, in different sections of the IUD of this invention, in order to provide for the controlled release, at different rates if desired, of different medications.

Also, to increase the efficacy of properly situated IUDs, the silicone elastomer can include a sufficient amount of an anti-fertility material, as noted above. This would be released uniformly and gradually during a prolonged period of time of months or even years and further increase the efficacy of IUDs in preventing conception. The advantage of this uterine introduction of anti-fertility agent over oral ingestion is that the oral form requires daily usage and motivation and can be forgotten or "skipped".

It is also within the purview of this invention to construct the IUD totally of a silicone elastomer of suitable resilience, flexibility and plastic memory, and which is medically acceptable and biologically inert, has a low hemolysis index and non-wetting surface property. The non-wetting surface helps to reduce incrustation with calcium salts, such as calcium carbonate, and consequent clotting, which is somewhat of a problem when polyethylene is used.

The inserting instrument, for inserting the IUD of this invention into the patient, is best seen in FIG. 7. The inserting instrument itself, which is generally designated by numeral 80, comprises an elongated hollow tube 82 and a plunger member 84 for discharging the IUD 10 from a position within the tube 82 into the uterus.

The tube 82, in the preferred embodiment, is approximately 196 mm. from the distal end 86 to the finger rest 88 which is located at the proximal end of the tube 82. Mounted peripherally about the tube 82 and spaced approximately 45 mm. from distal end 86 in a horizontal flange 90, the purpose of which is to limit the degree of insertion of the tube into the uterus, to prevent excess penetration of the insertion instrument and possible harm to the patient. The plunger 84 comprises a stem 92, a piston 94, mounted at the distal end of the stem, and a handle 96, mounted at the proximal end of the stem. The proximal ends of filaments T are fastened to stem 92 or piston 94 of plunger 84, as by tieing, fusion or a suitable adhesive and a substantial length of filaments T resides alongside stem 92 of plunger 84 and readily unwinds as the inserting device is removed from the uterus after the IUD 10 is inserted. A clearance is provided between plunger piston 94 and the inner diameter of insertion tube 82 to permit easy movement of the plunger in the tube, thereby allowing for the presence of the filament therein.

The tube 82 and piston 94 of plunger 84 are preferably of rounded-corner rectangular cross-section, having a width of about 6 mm. and a depth of about 4 mm. and a wall thickness of about 0.5 mm. The piston 94 of plunger 84 has a width of about 3 mm., a depth of about 2 mm. and a length of approximately 202 mm. The foregoing dimensions are optimum, but are not critical, and will be varied to accommodate the particular shape and dimensions of the IUD being inserted.

For example, if the IUD 10 is of elliptical cross-section, the insertion tube 82 and piston 94 will also be of elliptical cross-section.

The inserting instrument 80 is desirably molded of a medically acceptable material, such as medical grade polytetrafluoroethylene.

In practice, the IUD 10 is packaged in package 12 with the inserting instrument 80, in the manner shown in FIG. 7, but preferably not with the proximal end of the preferred embodiment of the IUD partially inserted into the distal end of 86 of tube member 82. The reason for not inserting the IUD 10 into the tube in packaging, is to avoid any loss of plastic memory of the convolute section 36 and 38 and the legs 20 and 22 of the IUD.

The IUD and inserting device are packaged in a hermetically sealed, sterilized container 12, of a well-known type of material and in a manner which is well-known in the art, such as by forming the container, evacuating the container, replacing the interior of the container with a sterilizing atmosphere such as ethylene oxide gas, evacuating that gas and then completing the sealing of the container.

In use, the IUD of this invention is inserted as follows. The usual time period for the insertion of the intrauterine device would be during the last day or two of a normal menstrual period. Prior to inserting the IUD, the physician or other medical professional, by history and pelvic examination of the patient would consider the contraindications to its use. The most important such contraindications are suspicion of pregnancy or actual pregnancy, acute cervicitis, acute salpingitis, suspected carcinoma, distortion of uterine cavity by fibroids, septate or bicornuate uterus, or menorrhagia or unexplained bleeding. When none of the contraindications to the use of the IUD is present, the patient's legs are inserted in stirrups on the examining table in the usual pelvic examination position, and the physician may do another pelvic examination to confirm the size and position of the uterus and confirm the diagnosis of anteflexion or retroflexion and the depth of the uterine cavity. Subsequently, the cervix would be cleaned with an antiseptic solution, applying a long (190 mm.) tenaculum to the anterior lip of the cervix and sounding the uterus with a sterile sound. Prior to dilating and/or sounding, a sterile local anesthetic may, if desired, be applied to the cervix and cervical canal to eliminate discomfort.

For insertion of the intrauterine device, the sterile package 12 would first be opened by the physician's or medical professional's assistant. Using sterile gloves, the insertion device 80 would be held in one hand, and the other hand would compress and insert the legs 20 and 22 of the IUD 10 into the open distal end of the tube 82. Plunger 84 would then be pulled outwardly, so that the filaments T, which are attached at one end to IUD 10 and at the other end to the plunger 84, and the slack of which is located beside stem 92, would be used to pull the body of the intrauterine device 10 down into the tube 82. The plunger would be pulled inwardly until all but the bulbous end 56 of the intrauterine device 10 has been drawn into the tube 82, making sure that both the IUD and the flat surface of the insertion tube flange 90 are in a horizontal plane, to insure proper placement of the IUD in the frontal plane of the uterine cavity. Of course, when located in the insertion tube, the convolute sections 36 and 38 of the intrauterine device 10 would be straightened out and would be substantially coextensive with shank 16. Preferably, the IUD 10 is not inserted into the insertion tube 82 until one or two minutes prior to use, in order not to interfere with the "memory" of the intrauterine contraceptive device.

Figure 1:
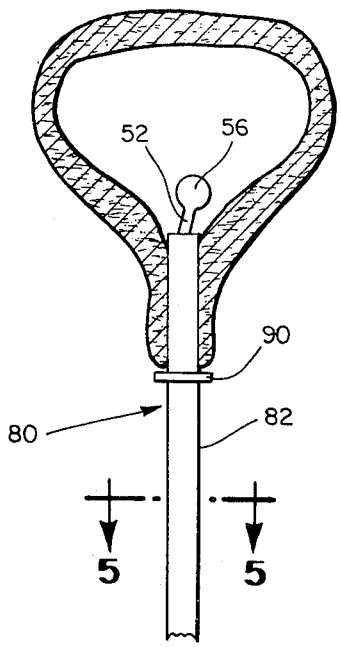
FIG. 1 is a front elevational view of the IUD of this invention, located in the tubular insertion device and inserted in the uterus for introduction of the IUD in utero.

The tenaculum would be slightly pulled on by the physician to straighten out the uterine canal and give a slight counter-pressure. Gently and slowly, the insertion device 80 would be inserted into the cervical os until the flange 90 reaches the anterior edge of the cervical os and the insertion device is in the position shown in FIG. 1. The plunger 84 is then pushed gently and slowly into the tube 82, as far as it will go. As the IUD 10 is introduced into the frontal plane of the uterine cavity by the movement of plunger 84, it regains its original configuration, as illustrated in FIG. 2 and is properly emplaced within the uterine cavity. The inserting unit 80 is then withdrawn from the cervical canal, and the tail T of the IUD is pulled out from alongside stem 92 and is then cut, leaving approximately 75 mm. of the tail attached to IUD 10 and extending into the vagina.

Of course, any instruments used to assist in the insertion of the IUD should be removed. Once the IUD has been properly inserted, the patient's legs may be straightened out, and the patient should be allowed to rest for a few minutes after the insertion.

In the event that the IUD is desired to be removed at any time, the physician may grasp the proximal end of the tail T with a uterine dressing forceps or sponge forceps, and pull outwardly with steadily gentle force. This would tend to pull the legs 20 and 22 of the IUD inwardly, so that the IUD can gently be withdrawn from the uterus. The convolutes 24 and 26 will straighten out, for ease of withdrawal, as the IUD is pulled through the cervix.

Figure 3:
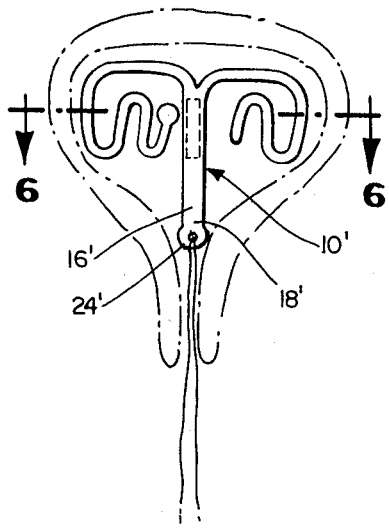
FIG. 3 is a view, similar to FIG. 2, showing a second embodiment of the invention.

The IUD 10' illustrated in FIG. 3 is identical to the IUD 10 of FIG. 2, with the sole exception that the shank 16 terminates, at its proximal end 18, in a small round nubbin 24', to which the filaments T are tied or otherwise fastened. Therefore, IUD 10' does not have divergent legs which assist in preventing its accidental expulsion. In use, the IUD 10' of FIG. 3 is handled in the same manner as the IUD of FIG. 2, with the exception that it may be desired to package the IUD 10' with the shank 16 extending into tube 82 of the inserting device, so that all that is required to be done to complete insertion of the IUD into the inserting device is to pull outwardly on knob 96 of plunger member 84 to straighten out convolute sections 36 and 38 and draw them into tube 82.

Figure 4:
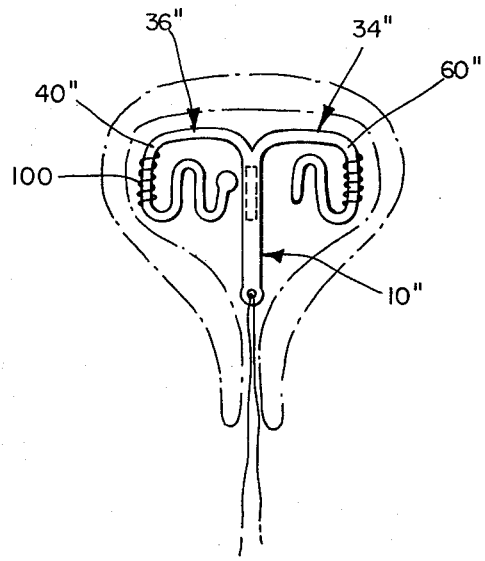
FIG. 4 is a view, similar to FIG. 3, showing yet another embodiment of the invention.

In the embodiment of FIG. 4, it will be seen that legs 40'' and 60'' of the respective convolute sections 36'' and 38'' of IUD 10'' are wrapped with copper wire 100. Copper wire 100 is of about 0.1 mm. diameter, and is of a length to provide at least 100 millimeters of surface area on each leg. The copper wire 100 is wound on each of the two legs 40'' and 60'' in a spiral winding. The function of the copper wire is to enhance the contraceptive effect of the IUD by inhibiting implantation of the blastocyst and by the tendency of copper to inactivate spermatozoa. Although copper wire is shown only on legs 40'' and 60'', if a greater amount of copper wire is desired, it may be wound on other segments of the convolutes 36'' and 38''. The copper wire may, if desired, be wound on other legs of the convolutes, instead of legs 40'' and 60''.

In the use of the IUD of this invention, in the event that the physician is attempting to locate the IUD, and the tail T has accidentally been lost, the physician may locate the IUD in utero, without the need for X-rays, by the insertion of a ferrous "sound," a well-known instrument, into the uterus and by detecting, by feel, the pull of the permanent magnet 28 on the ferrous sound. An electromagnet or a magnetic sound of reverse polarity from that of the proximal end of magnet 28 may also be used to facilitate the location and the removal of a "lost" IUD or, under certain conditions, an IUD which has pierced the wall of the uterus.

Figure 8:
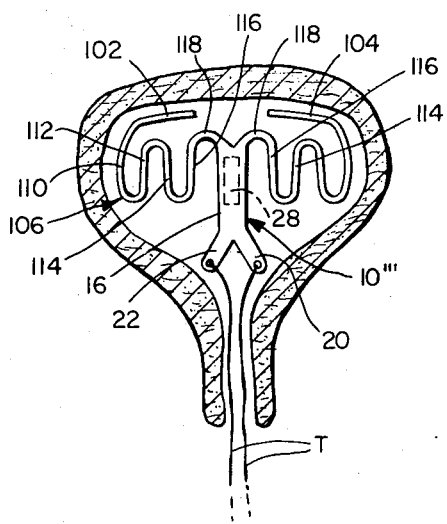
FIG. 8 is a front elevational view, similar to FIG. 2, showing yet another embodiment of the invention where the convoluted loops are fastened directly to the shank.

The embodiment of IUD illustrated in FIG. 8 is substantially identical to that illustrated in FIG. 2, with the sole exception that there is no transverse arm connecting the convoluted portions to the shank, and one of the convoluted portions does not end in a bulbous member. Rather, in the embodiment of FIG. 8, IUD 10''' is formed of a shank member 16, which is identical with the shank member illustrated in FIG. 2, and contains embedded therein the permanent magnet 28. Shank 16 terminates at its lower end in the bifurcated legs 20 and 22, which have apertures formed therein through which the threads T are fastened to extend from the uterus into the vagina, to facilitate removal of the IUD.

The IUD''' possesses two transversely extending arms 102 and 104, but unlike the counterpart arms of FIG. 2, these are not directly connected to the shank 16. Rather, the outer ends of the arms 102 and 104 are connected to the convoluted loop sections, generally designated 106 and 108, each of which comprises four interconnected vertical segments designated 110, 112, 114 and 116. The vertical section 116 which is closest to the shank is connected to the shank by connecting member 118.

The embodiment of FIG. 8 functions in the identical manner as that of FIG. 2, the convoluted portions being capable of straightening out when the IUD is inserted in the applicator 80 for insertion into the uterus. The convoluted portions 106 and 108 fill the uterus in the same optimal fashion as described with respect to the embodiment of FIG. 2, and because more convolutes are present in this embodiment, do a somewhat better job of filling the uterus. It will be appreciated that the end of horizontal members 102 and 104 will have to be curved, so as not to present any sharp surface which will in any way damage the uterus.

Figure 9:
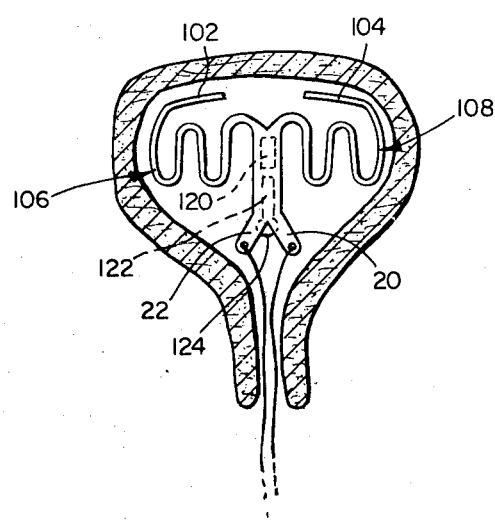
FIG. 9 is a view similar to FIG. 8, but including means for the sustained release of liquid medication.

The embodiment of FIG. 9 is identical with that of FIG. 8, except that the shank contains a shorter magnet 120 formed therein to allow for the medicament container which is formed with the IUD itself. The medication container is formed as a latex sleeve 122 located and formed in the bottom portion of the shank 16, and terminating in the Silastic globule portion 124 which extends beneath the shank and between the arm 20 and 22.

Figure 10:
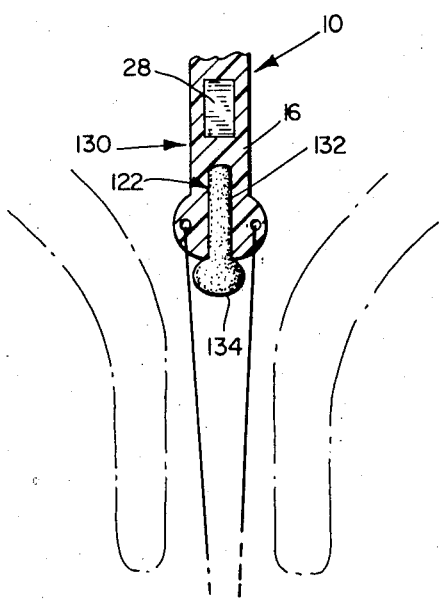
FIG. 10 is a partial cross-sectional view of yet another embodiment of the invention, similar to that of FIG. 3, but including means for the sustained release of liquid medication.

FIG. 10 illustrates another embodiment of the invention, similar to that illustrated in FIG. 9, except that the IUD 130 does not terminate in bifurcated arms. Rather, in the manner illustrated in FIG. 3, the IUD merely terminates in the elongated shank. FIG. 10 better illustrates the manner in which the medication container 122 is formed in the end of the shank 16. It will be appreciated that the incorporation of the container into the shank of FIG. 10 is substantially the same as its incorporation into the shank of FIG. 9, with the exception that in the embodiment of FIG. 9, the globule is partly seated in suitable cut-outs from the bifurcated arms 20 and 22. Moreover, it is to be understood that the embodiment of FIG. 10 can be used with either of the arm configurations illustrated in FIG. 2 and FIG. 8.

The medicament container 122, which is formed in shank 16 has an elongated cylindrical portion 132, which is formed of latex. At the lower end of the cylindrical section 132 is the globular section 134, which is formed of Silastic material, the silicone elastomer described above. The medicament container may be prefilled with medicament, prior to insertion into the shank of the IUD, such as by leaving the upper end of the container open, and subsequently capping it with an end cap of latex which is heat or solvent sealed closed. Alternatively, because the Silastic material is resealable, after the container has been inserted and mounted or formed in the IUD, the medicament can be introduced into the container 122 by the introduction of a fine hypodermic needle into the Silastic globule 134 for the purpose of introducing the appropriate quantity of medication, of the desired concentration, into the globule. The latex container portion may be pre-formed and mounted in the shank by the use of a suitable adhesive or solvent.

Because of the unique characteristic of the Silastic material, it will gradually release medicament contained in the container 122 into the surrounding body cavity. Therefore, in the embodiment illustrated in FIG. 10, whatever medicament is contained within the container 122 will be released into the "mouth of the womb" proximate the entrance of the uterus. A certain amount of this medication will migrate through the cervix into the vagina in the normal body fluids.

The use of the IUD containing medication in prolonged release form is particularly desirable from the standpoint of the prevention and cure of venereal diseases, such as syphilis and gonorrhea, which are extremely widespread, and which present an enormous health hazard of epidemic proportions. It is well known that syphilis and gonorrhea organisms and other venereal disease-causing organisms can be killed or controlled by the use of suitable antibiotics or antibacterial agents, such as penicillin, erythromycin, rifampicin, tetracycline, doxycycline and gentamycin. Thus, by the gradual release of one of these antibiotics in situ, the syphilis or gonorrhea organisms present in the vagina or the uterus will be killed by the medication before they have an opportunity to grow.

The container 122 is filled with a quantity and concentration of a suitable antibiotic or antibacterial agent which will provide a continuous and sustained release of the agent during a period of about one to about six months, it being understood that the instantaneous amount of agent released from the container need only be small, because of the cumulative effect of the release over a substantial period of time, and the minimum inhibitory dose of a drug, administered to a specific tissue target area, such as the uterus or vagina, is small.

The rate of release and duration of release of the medicament can be controlled by regulating the concentration of the medicament, the volume of medicament in the container 122, the size of the surface area of globule 134, and the thickness of the globule wall. Thus, these factors can be varied to suit the particular needs of the patient to provide for given rates of release and periods of release of the various medications.

In addition to the antibiotics described, it is also within the purview of this invention to incorporate in the container 122 an acid, such as lactic acid, which is known to be hostile to the gonococcus but is not injurious to the patient.

It is to be noted that with respect to any of the medicaments utilized, it will be necessary to have present in the vagina the minimum inhibitory concentration of the medication sufficient to cause the inactivation or inhibition of the growth of the gonococcus organism or other venereal disease-causing organism to cause its destruction or disintegration. Among the various gonococcus strains, the resistance of these strains to various medications can vary. In particular, the strains present in the Far East, such as the *Neisseriae gonococcus* are more resistant to treatment by medication than are the organisms which are indigenous to the western hemisphere. Accordingly, with respect to the more resistant organisms, it will be necessary to present a greater concentration of medication in container 122. It will, therefore, be appreciated that, when the IUDs of the invention are manufactured for use in different countries, they would be manufactured with a construction and medication which is designed to release the minimum inhibitory concentration of medication for the particular gonococcal organism in the area in which the IUD is to be used.

Once the IUD has been inserted in the uterus of the user, the medication in the container will be distributed during a period of from one month to six months or even one year. The particular period of release will be indicated on the package for the IUD, so that the physician can know when the effect of the medication will cease, and will advise the patient that it will be necessary to come into the physician's office for a reintroduction of medication into the IUD a reasonable period of time before the exhaustion of the contents of the container. Because the Silastic can be manufactured to be self sealing, new medication can be introduced by the physician by the utilization of a hypodermic syringe containing the desired volume of medication, and using a relatively fine needle, such as a 24, 25 or 26 gauge hypodermic needle. An hypodermic syringe with an appropriate size of needle and containing the necessary medication, in a quantity sufficient to fill the container 122 of the IUD can be prepackaged for disposable use for this purpose. In the instance of the embodiment illustrated in FIG. 10, the physician, in order to introduce the medication into the globule, would have to insert a vaginal speculum into the patient to expose the surface of the IUD, and pull down gently on the vaginal filaments T of the IUD until the globule 134 is exposed. The surface of globule 134 would then be painted with a suitable antiseptic solution, such as aqueous Zephiran or Betadine solution, after which the hypodermic syringe could be utilized to recharge the container 122 of the IUD.

Figure 11:
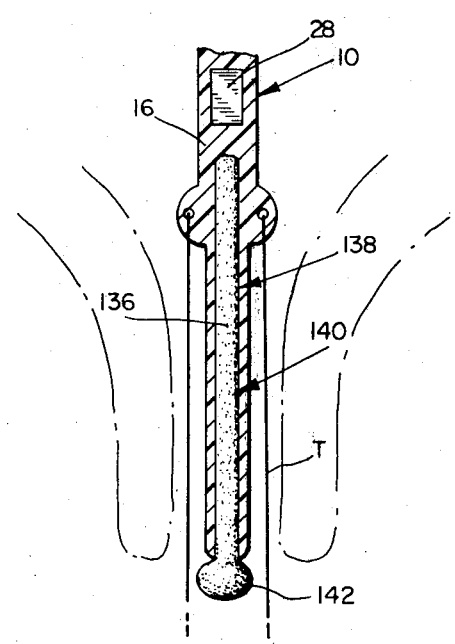
FIG. 11 is a view similar to FIG. 10, but with an elongated shank extending through the cervix for the direct release of medication into both the vagina and uterus.

FIG. 11 shows yet another embodiment of the invention which avoids some of the limitations of FIG. 10, in that the embodiment of FIG. 11 contains an elongated shank having a section 138, which is part of the shank, and which extends through the cervix and opens into the vaginal cavity itself. The outer diameter of this elongated section 138 is somewhat less than the outer diameter of the upper portion of the shank 16, which resides in utero, and the proximate end of the extension 138 extends into the vagina. Similar to the embodiment of FIG. 10, this IUD contains a latex container 140 for a suitable medication, and, because of the greater length of the extended shank 138, is capable of holding a substantially greater amount of medication for release into the vagina. As is seen in FIG. 11, the globule 142 of Silastic material located at the proximate end of the shank extension 138 extends into the vagina, so that the medication for the control of the gonococcus or syphilis organism is more readily available in the vagina itself for purpose of killing the organism before it enters the cervix and to insure a maximum concentration of medication in the vagina per se.

The embodiment of FIG. 11 facilitates the introduction of additional medication into the container in the situation where the container is exhausted or almost exhausted, because with this embodiment it is not necessary to pull the IUD down from the cervix to expose the globule below the entrance to the cervix. Consequently, when it is desired to refill the embodiment of FIG. 11, it is merely necessary to cleanse the globule 142 with an antiseptic solution and subsequently to inject the charge of refill medication into the container.

It is to be noted that both embodiments of FIGS. 10 and 11 desirably retain, located within the shank, the magnet 28, as described above, for the purpose of facilitating the location of the IUD, in utero, with the use of a ferrous sound.

Figure 12:
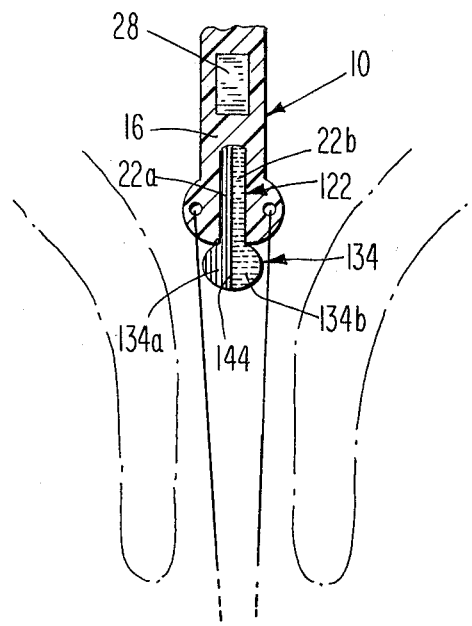
FIG. 12 is a view similar to FIG. 10 of another embodiment wherein the sustained release means is compartmented.

Viewing FIG. 12, there will be seen yet another embodiment of the invention, similar to that seen in FIG. 10. The only difference between the embodiment of FIG. 12 and that of FIG. 10 is that the compartment 22 in the embodiment of FIG. 12, is divided by latex barrier member 144, into two separate parts. Both the globule portion 134 and the cylindrical portion 132 are thus formed into two discrete parts chambers. The cylindrical segments of the compartments are referred to by the designations 132a and 132b, whereas the globular sections are referred to as 134a and 134b. By the use of this construction, the medication container 122 is able to contain two different medications.

In the use of the apparatus of the invention and the practice of the process, it is desirable to be able to release a trichomonacide or moniliacide to prevent, treat or cure trichomonas vaginalis or moniliasis, immediately as they are transmitted in order to prevent any of these conditions from developing in the host individual. A trichomonacide or moniliacide can be inserted in the compartment formed by sections 132a and 134a, and would be gradually released into the lower portion of the uterus at the globular section 134a. When it is desired to refill that section of the container, a fine hypodermic needle can be inserted into the proper section of the resealable Silastic globule to insert additional medication.

In similar fashion, another medication can be inserted in the other portion of the container 122, and defined by cylindrical portion 132b and globule portion 134b. In the embodiment of the invention in which medication is released over a prolonged period of time for the prevention or cure of gonorrhea or other venereal disease, a suitable antibiotic can be inserted in that compartment. The antibiotic would be present in such a quantity that, considering the size and physical characteristics of the container and globule, and the concentration of the medication, the minimum inhibitory amount of the medication is released into the lower end of the uterus during a prolonged period of time.

Figure 13:
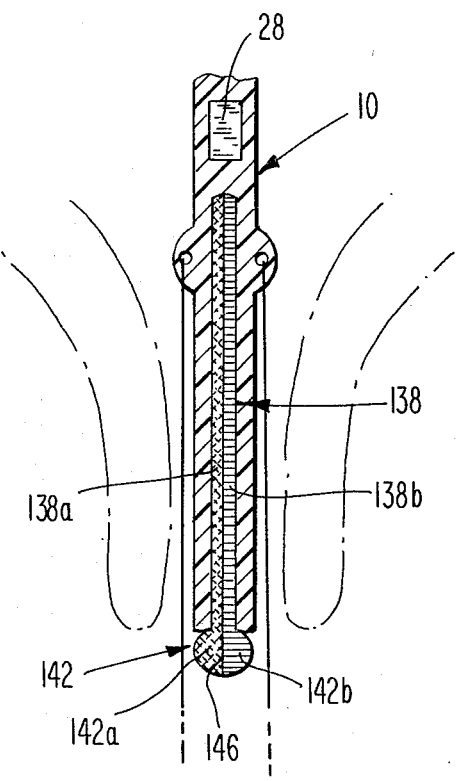
FIG. 13 is a view similar to FIG. 11 of another embodiment wherein the sustained release means is compartmented.

The embodiment of FIG. 13 is similar to that of FIG. 11, with the exception that, like in the embodiment of FIG. 12, the container 138 is divided into two compartments by the barrier wall 146. The two cylindrical compartments are respectively referred to as 138a and 138b and the globular compartments are referred to as 142a and 142b. The compartment formed by portions 138a and 142a can be used, for example, for the storage and sustained release over a prolonged period of time of a trichomonacide or moniliacide, and the other compartment, formed by portions 138b and 142b can contain a suitable antibiotic, for example, for sustained release in minimum inhibitory quantities, in order to prevent, treat or cure venereal disease.

It will be seen from FIG. 13, as is the case in the embodiment of FIG. 11, that the globule end of the refillable container extends beyond the proximal end of the cervix into the vagina. This construction has two major benefits. First of all, the greater length of container permits storage of a greater quantity of medication, thereby increasing the times between refillings of the container. Secondly, by having the globule actually present inside the vagina, greater access to the globule 142 for the purpose of refilling the container sections is provided. This embodiment also facilitates the release of antibiotic or other suitable medication directly into the vagina, the site at which it is most desirable to have medication present in order to prevent, treat or cure any venereal disease.

It will be appreciated that the container constructions illustrated in FIGS. 10, 11, 12 and 13 can be used in connection with other constructions of IUD devices than those described and claimed herein. For example, any IUD can be formed with an elongated shank and which serves as the site of the container 122 for storage and release of suitable medicament. Accordingly, it is within the purview of this invention, to incorporate the container features of the invention in an IUD other than one of the embodiments illustrated in FIGS. 1 to 9 inclusive. It is further within the purview of this invention to incorporate the concept of the release of antibiotics and/or medicaments to combat gonorrhea, syphilis, trichomonas, vaginalis and moniliasis in an IUD other than one of the embodiments illustrated herein.

In the process of the invention, an intrauterine contraceptive device is inserted in the uterus, and contemporaneously therewith, a quantity of analgesic is released into the uterus, to desensitize the uterus and minimize likelihood of expulsion of the IUD, and a trichomonacide or moniliacide into the cervix, and vagina, over a prolonged period of time, and contemporaneously a minimum inhibitory quantity of an antibiotic is also released into the uterus, cervix and vagina for the prevention, treatment and cure of venereal diseases.

It is noteworthy that, instead of prefilling and packaging, in the prefilled stage, each IUD in accordance with this invention, the IUDs could be sold sterilized and packaged, with the containers unfilled. This would allow the physician, immediately prior to insertion of the IUD into the patient, to select an appropriate trichomonacide or moniliacide and/or antibiotic to be incorporated into the compartment or compartments of the container portion of the IUD, in order to suit the medication and quantity to the particular needs of the patient, and the particular environment of the physician. For example, in those geographic areas where a more virulent strain of gonococcus is present than in others, a greater concentration of antibiotic would be incorporated into the container 122, in order to insure that the minimum inhibitory quantity for that particular strain is released into the patient.

What is claimed is:

1. A process operative over a prolonged period of time for the contemporaneous prevention of conception and the prevention, treatment or cure of venereal disease by the use of a single apparatus comprising an intrauterine contraceptive device and an integral reservoir adapted to extend into the vagina of a human female comprising the steps of:
 a. Inserting into the uterus of a human female a safe and effective intrauterine contraceptive device;
 b. Substantially contemporaneous with the insertion of such device, releasing into the uterus an anesthetic in a quantity sufficient to anesthetize the uterus to prevent expulsion of said device;
 c. Continuously releasing said anesthetic directly into the uterus over a prolonged period of time of at least about thirty days while said device is resident in said uterus to continue to anesthetize the uterus and prevent expulsion of said device;
 d. Substantially contemporaneous with the insertion of said device into the uterus, commencing the release directly into the vagina of the minimum inhibitory dosage of at least one medication for the prevention, treatment or cure of venereal disease in the human female; and
 e. While said device is resident in said uterus, continuously releasing directly into the vagina the minimum inhibitory dosage of such medication over a prolonged period of time of at least about thirty days.

2. A process as set forth in claim 1, including the step of refilling said reservoir in situ to insert an additional quantity of at least one medication to provide controlled release of the minimum inhibitory dosage of said medication over an additional continuous period of time of at least about thirty days.

3. A process as set forth in claim 2, wherein said reservoir is refilled by the resealable introduction of a hypodermic needle therein.

4. A process as set forth in claim 1, wherein at least two medications are released directly into the vagina.

5. A process as set forth in claim 1, wherein at least one medication is an antibiotic.

* * * * *